US012662448B2

(12) United States Patent
Vanwonterghem et al.

(10) Patent No.: US 12,662,448 B2
(45) Date of Patent: Jun. 23, 2026

(54) METHOD TO PRODUCE A UREA AMMONIUM SULPHATE-BASED COMPOSITION

(71) Applicant: Yara International ASA, Oslo (NO)

(72) Inventors: Yumi Vanwonterghem, Zaventem (BE); Pieter Vidts, Gentbrugge (BE)

(73) Assignee: YARA INTERNATIONAL ASA, Oslo (NO)

( * ) Notice: Subject to any disclaimer, the term of this patent is extended or adjusted under 35 U.S.C. 154(b) by 874 days.

(21) Appl. No.: 18/007,575

(22) PCT Filed: Jun. 9, 2021

(86) PCT No.: PCT/EP2021/065381
§ 371 (c)(1),
(2) Date: Dec. 1, 2022

(87) PCT Pub. No.: WO2021/250050
PCT Pub. Date: Dec. 16, 2021

(65) Prior Publication Data
US 2023/0219885 A1     Jul. 13, 2023

(30) Foreign Application Priority Data

Jun. 9, 2020     (EP) .................................... 20179014

(51) Int. Cl.
*C07C 273/02*          (2006.01)
*B01J 19/26*           (2006.01)
*C01C 1/242*           (2006.01)

(52) U.S. Cl.
CPC ............. *C07C 273/02* (2013.01); *B01J 19/26* (2013.01); *C01C 1/242* (2013.01); *B01J 2219/00119* (2013.01)

(58) Field of Classification Search
None
See application file for complete search history.

(56) References Cited

U.S. PATENT DOCUMENTS 3,928,015 A * 12/1975 Siegel ....................... C05C 3/00
                                                      71/28
8,524,165 B2 * 9/2013 Ledoux .................... B01J 19/26
                                                      422/224

(Continued)

FOREIGN PATENT DOCUMENTS

CA          3093750          9/2019
CN        101006011 A        7/2007
(Continued)

OTHER PUBLICATIONS

Chinese Office Action (including English language translation) issued in App. No. CN202180038454, dated Oct. 13, 2023, 18 pages.

(Continued)

*Primary Examiner* — Amy C Bonaparte
(74) *Attorney, Agent, or Firm* — Dilworth IP, LLC

(57)          ABSTRACT

The present disclosure is related to a pipe reactor. In its broadest aspect, the present disclosure is related to a method for producing a urea ammonium sulphate-based composition in a pipe reactor comprising a first and a second mixing zone. The method comprises the steps of: a) directing a liquid stream comprising ammonium bisulphate to the first mixing zone of the pipe reactor; b) directing a first stream of ammonia to the first mixing zone of the pipe reactor for reacting with the liquid stream comprising ammonium bisulphate, provided in step a), to obtain a liquid stream comprising ammonium sulphate; c) directing the liquid stream comprising ammonium sulphate, provided in step b), to the second mixing zone of the pipe reactor; and d) directing a liquid stream of urea to the second mixing zone of the pipe reactor for mixing with the liquid stream comprising ammonium sulphate.

10 Claims, 1 Drawing Sheet

(56)                    References Cited

U.S. PATENT DOCUMENTS

| | | | |
|---|---|---|---|
| 11,993,557 B2 * | 5/2024 | Van Belzen | ............. B01J 4/002 |
| 2008/0092614 A1 | 4/2008 | Ingels | |
| 2008/0145283 A1 * | 6/2008 | Ledoux | .................... C05C 3/00 |
| | | | 422/600 |
| 2017/0348658 A1 * | 12/2017 | Littmann | ................ C08F 6/001 |
| 2019/0276325 A1 | 9/2019 | Bruno | |

FOREIGN PATENT DOCUMENTS

| | | | |
|---|---|---|---|
| CN | 101132988 | A | 2/2008 |
| CN | 104177236 | B | 10/2015 |
| DE | 10133935 | A1 | 1/2003 |
| EP | 1861335 | A1 | 12/2007 |
| EP | 3542899 | A1 | 9/2019 |
| IT | 201600115907 | A1 | 5/2015 |
| WO | 2019180066 | | 9/2019 |

OTHER PUBLICATIONS

International Search Report and Written Opinion issued in App. No. PCT/EP2021/065381, mailing date Sep. 3, 2021, 14 pages.

Office Action received for Russian Patent Application No. 2022129471, mailed on Aug. 8, 2024, 8 pages English translation only.

* cited by examiner

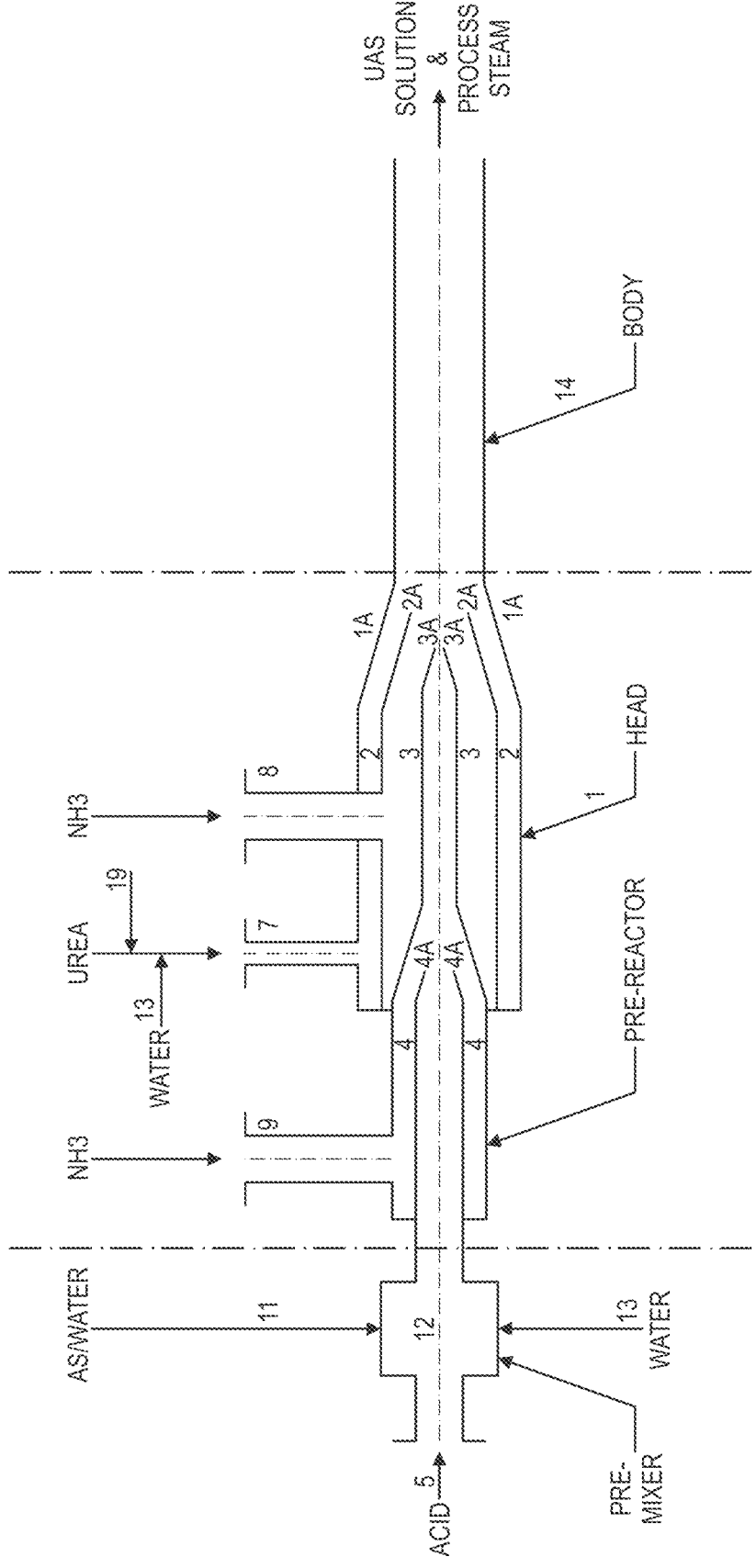

METHOD TO PRODUCE A UREA AMMONIUM SULPHATE-BASED COMPOSITION

FIELD OF THE INVENTION

The present disclosure is related to a method for the manufacture of a urea ammonium sulphate-based composition, in particular in a pipe reactor.

BACKGROUND OF THE INVENTION

Urea ammonium sulphate (UAS) is a common fertilizer. UAS may be produced as a solution (up to about 11 weight % of ammonium sulphate (AS) can be dissolved into a urea melt) or a slurry (when a urea melt comprises more than about 11 weight % of AS) before granulation using a tank type reactor or a pipe reactor (see e.g. EP1781569 B1, EP1861335 B1 and WO2019180066).

In a pipe reactor, a liquid stream comprising ammonium bisulphate ($NH_4HSO_4$), which may be prepared in a mixing tank or another pipe reactor, is mixed with a stream of gaseous ammonia to obtain a stream comprising ammonium sulphate (($NH_4)_2SO_4$), to which is mixed with a liquid stream comprising urea to obtain a solution comprising urea and ammonium sulphate.

However, it was observed that, under standard operating conditions, the urea added to the pipe reactor started to crystallize inside the reactor, which increased the viscosity of the solution comprising urea and ammonium sulphate and the pressure in the pipe reactor. The increased viscosity and pressure made the production process challenging to run on a continuous basis.

SUMMARY OF THE INVENTION

Surprisingly, it was found out that it was possible to eliminate or at least reduce the crystallization of urea by pre-heating the stream of ammonia that is mixed with the solution comprising ammonium bisulphate before the stream of ammonia is directed in the pipe reactor.

In its broadest aspect, the present disclosure is related to a method for producing a urea ammonium sulphate-based composition in a pipe reactor comprising a first and a second mixing zone. The method comprises the steps of:
  a) directing a liquid stream comprising ammonium bisulphate to the first mixing zone of the pipe reactor;
  b) directing a first stream of ammonia to the first mixing zone of the pipe reactor for reacting with the liquid stream comprising ammonium bisulphate, provided in step a), to obtain a liquid stream comprising ammonium sulphate;
  c) directing the liquid stream comprising ammonium sulphate, provided in step b), to the second mixing zone of the pipe reactor; and
  d) directing a liquid stream of urea to the second mixing zone of the pipe reactor for mixing with the liquid stream comprising ammonium sulphate, provided in step b), to obtain a urea ammonium sulphate-based composition; wherein, in step b), the temperature of the first stream of ammonia directed to the first mixing zone of the pipe reactor is at least 100° C.

BRIEF DESCRIPTION OF THE FIGURES

The following description of the FIGURE of a specific embodiment of a system according to the present disclosure is only given by way of example and is not intended to limit the present explanation, its application or use. In the FIGURE, identical reference numerals refer to the same or similar parts and features.

The FIGURE represents a reactor for the production of UAS according to the present disclosure comprising a pipe reactor, a pre-mixer and a pre-reactor, being also a pipe reactor.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

All references cited in this description are hereby deemed to be incorporated in their entirety by way of reference.

As used herein, the following terms have the following meanings:

"A", "an", and "the" as used herein refers to both singular and plural referents unless the context clearly dictates otherwise. By way of example, "a stream" refers to one or more than one stream.

"About" as used herein referring to a measurable value such as a parameter, an amount, a temporal duration, and the like, is meant to encompass variations of +/−20% or less, in particular +/−10% or less, more in particular +/−5% or less, even more in particular +/−1% or less, and still more in particular +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "weight percent", "% wt" or "weight %", here and throughout the description unless otherwise defined, refers to the relative weight of the respective component based on the overall weight of the formulation.

In its broadest aspect, the present disclosure is related to a method for producing a urea ammonium sulphate-based composition in a pipe reactor comprising a first and a second mixing zone.

The method comprises the steps of:
  a) directing a liquid stream comprising ammonium bisulphate to the first mixing zone of the pipe reactor;
  b) directing a first stream of ammonia to the first mixing zone of the pipe reactor for reacting with the liquid stream comprising ammonium bisulphate, provided in step a), to obtain a liquid stream comprising ammonium sulphate;
  c) directing the liquid stream comprising ammonium sulphate, provided in step b), to the second mixing zone of the pipe reactor; and d) directing a liquid stream of urea to the second mixing zone of the pipe reactor for mixing with the liquid stream comprising ammonium sulphate, provided in step b), to obtain a urea ammonium sulphate-based composition; wherein, in step b), the temperature of the first stream of ammonia directed to the first mixing zone of the pipe reactor is at least 100° C.

A pipe reactor according to the disclosure is a device comprising a tubular body and a reactor head, wherein the reactor head has means for axial injection of acid and means for injection of ammonia. The ammonia can be free and/or bound and/or mixed. Further it has means for supply of a third stream, for example a liquid stream comprising urea, and a reaction chamber where acid and ammonia react with each other to form a stream comprising ammonium salts, for example ammonium sulphate, before coming into contact with the third stream. The pipe reactor could also be used for reacting another acid and base with other heat and/or acid sensitive component than urea.

In one embodiment, the pipe reactor used in the method according to the present disclosure is a pipe reactor as disclosed in EP1861335B1 and EP1781569B1, which are both incorporated herein by way of reference, and which may be used in combination with a granulator, in a method for producing a solid UAS composition, in particular as disclosed in EP1781569B1. The use of a pipe reactor allows for the production process to be a continuous process, with relative short retention time in the reactor, resulting in less decomposition. Further advantages are a high degree of mixing, flexible in operation, low investment cost, low static loads on the building structure and/or easy to replace when corroded. The continuous process also makes it easy to couple the reactor to an on-site continuous process for one or more of the starting materials such as ammonia and/or ammonium carbamate or urea.

In one embodiment, the pipe reactor comprises a tubular body and a reactor head, wherein the reactor head comprises (i) means for axial injection of sulphuric acid, (ii) means for injection of ammonia and/or ammonium carbamate, (iii) means for supplying a urea solution; and (iv) a reaction chamber, wherein the means for axial injection of sulphuric acid has a first cone, the means for injection of ammonia and/or ammonium carbamate comprise an inlet, has a second cone at its downstream end, and forms a first annular chamber surrounding the means for injection of sulphuric acid, the means for supplying a urea solution comprise an inlet, has a convergent part at its downstream end, and forms a second annular chamber surrounding the means for injection of ammonia and/or ammonium carbamate; and the reactor chamber is substantially formed by the zone between the end of first cone and the end of the second cone, wherein the pipe reactor further comprises means for supplying an additive in the urea solution. The liquid stream comprising ammonium bisulphate and directed to the first mixing zone of the pipe reactor comprises ammonium bisulphate ($NH_4HSO_4$) in a solvent, in particular water. Ammonium bisulphate is obtained by the reaction of one mole of ammonia with one mole of sulphuric acid. The bisulphate ion is an amphoteric substance, meaning it can react as an acid and a base. The liquid stream comprising ammonium bisulphate may also comprise ammonia and/or sulphuric acid. For example, ammonium bisulphate may be prepared with a small excess of ammonia, and the resulting stream comprising ammonium bisulphate comprises ammonia. However, even if the presence of an excess of ammonia, some residual sulphuric acid may be present in the liquid stream, for example if the liquid stream is not mixed well enough. Alternatively, the stream comprising ammonium bisulphate may be prepared with an excess of sulphuric acid, so the liquid stream comprising ammonium bisulphate may comprise sulphuric acid.

A first stream of ammonia is directed to the first mixing zone of the pipe reactor for reacting with the liquid stream comprising ammonium bisulphate. Ammonia reacts with ammonium bisulphate to provide ammonium sulphate. The first stream of ammonia may comprise other components, such as ammonium carbamate.

When confronted with the issue of urea crystallizing inside a reactor, several ways to remedy it may be envisaged, such as: (i) reducing the rate of injection of the liquid stream of urea, which would lower the ratio of urea/ammonium sulphate; (ii) increasing the water content of the mixture at the second mixing zone of the pipe reactor, which would cause a higher water content of the final stream of ammonium sulphate, thereby requiring more energy to evaporate the additional water; (iii) lowering the viscosity of the mixture in the pipe reactor with additives; (iv) raising the temperature of the mixture of the pipe reactor. Raising the temperature of the internal mixture was not seen as the approach with the highest chances of success since the mixture is already heated due to the heat released by the exothermic reaction between ammonia and sulphuric acid and between ammonia and ammonium bisulphate. It may be envisioned to raise the temperature of the internal mixture by different means, such as: (a) pre-heating the liquid stream of urea; (b) pre-heating the liquid stream of ammonium bisulphate; or (c) heating the pipe reactor from the outside.

When trying to solve the problem described above, it was found out that pre-heating the stream of ammonia before injecting it into the pipe reactor prevented the crystallization of urea and the subsequent viscosity of pressure build-up. The mechanism of action is not clear, it may be due to raising the temperature inside the pipe reactor, but other effects could also be envisioned, such as a change in the reaction profile in the reactor, or an improved mixing. Ammonia is a toxic compound with a boiling temperature of −33° C. and its use in chemical manufacturing is highly regulated, so heating up a stream of ammonia may raise technological challenges and associated safety issues. However, in the case of the present invention, the benefits outweigh these technological challenges.

It was discovered that when the temperature of the first stream of ammonia directed in a pipe reactor to at least 100° C., the reliability of the production operations is improved. It is not clear how an increased temperature of the first stream of ammonia reduces the viscosity of the stream in the pipe reactor. It may be envisioned that the hot stream of ammonia helps melting the crystals of urea formed in the pipe reactor. It may also be envisioned that the hot stream of ammonia increases the temperature of some surfaces of the pipe reactor, so that urea does not crystallized upon contact of these colder surfaces.

The first stream of ammonia may be heated in a number of ways known in the art. In one embodiment, steam may be used to heat up the ammonia. A plant of the production of urea ammonium sulphate often has a steam network as steam is required on other stages of the production. It is then easy to divert some of the stem from the existing steam network to heat up the stream of ammonia to the required temperature. The ammonia in the first stream of ammonia is in the gas phase. It may be directed to the pipe reactor at atmospheric pressure or higher pressure, for example, 5 bar.

It may also be envisioned to recover some heat from the pre-neutralization step of sulphuric acid to heat up the stream of ammonia.

The first stream of ammonia is regulated so that all the ammonium bisulphate and sulphuric acid comprised in the liquid stream comprising ammonium bisulphate is transformed into ammonium sulphate. Excess ammonia may easily be removed from the stream after the pipe reactor stage, so it may be preferred to operate the pipe reactor with an excess of ammonia.

In one embodiment, the temperature of the first stream of ammonia directed to the first mixing zone of the pipe reactor is at least 110, 115, 120° C. It was found that the temperature of the first stream of ammonia should be at least 100° C. to obtain suitable operating conditions in the pipe reactor. Further increasing the temperature of the first stream of ammonia, for example to at least 120° C., lead to an additional pressure drop compared to 100° C. It may be possible to increase the temperature of the first stream of ammonia beyond 120° C. However, additional heating increases the cost of production of the urea ammonium sulphate-based composition, so a compromise needs to be found between productivity, product quality and operating costs. In particular, it was found experimentally that a temperature of the first stream of ammonia of about 120° C. provided good working conditions.

The reaction between the first stream of ammonia and the liquid stream comprising ammonium bisulphate provides a liquid stream comprising ammonium sulphate. The liquid stream comprising ammonium sulphate may comprise the same additional components comprised in the first stream of ammonia and/or the liquid stream comprising ammonium bisulphate. In one embodiment, the stream comprising ammonium sulphate comprises aluminum sulphate. The liquid stream comprising ammonium sulphate comprises a solvent, which may be water.

The liquid stream of urea directed to the pipe reactor may comprise other components such as formaldehyde, biuret, ammonium sulphate, ammonia and mixtures thereof. These components may be residues, impurities, or by-products of the manufacturing process of urea. The liquid stream of urea may also comprise additives, such as granulation additives, that help the subsequent steps of the manufacturing process. In one embodiment, the liquid stream of urea may comprise a solvent and at least 80 weight % of urea. In particular, it may comprise at least 85 weight % of urea, in particular at least 90 weight % of urea. In one embedment, the liquid stream of urea is formed by adding water to a urea melt. In one embodiment, the solvent in the liquid stream of urea is water.

When the liquid stream comprising urea and the liquid stream comprising ammonium sulphate meet in the second mixing zone of the pipe reactor, some of the ammonium sulphate is solubilized in the liquid stream comprising urea. The two stream may partially or completely mix in the pipe reactor. Once the stream comprising urea ammonium sulphate is recovered at the end of the pipe reactor, it may be further mixed to obtain an homogeneous stream which may allow to produce homogeneous solid particles. The stream comprising urea ammonium sulphate may be processed according to standard practices known in the art before begin granulated. For example, if the water content is too high to produce solid particles, the stream may be dehydrated using a suitable process, for example a heat exchanger.

In one embodiment, the liquid stream comprising ammonium bisulphate is prepared in a pre-reactor fluidly connected to the pipe reactor, by reacting a stream of sulphuric acid, a stream of water and a second stream of ammonia. Since sulphuric acid is a strong acid and ammonia a weak base, the reaction of sulphuric acid with ammonia is very exothermic. The reaction consists in two steps: in the first step, a molecule of ammonia reacts with a molecule of sulphuric acid to form ammonium bisulphate, and in the second step, a second molecule of ammonia reacts with ammonium bisulphate to form ammonium sulphate. The high exothermicity of the reaction limits the rate of reaction that is achievable in a reactor because of the need to cool down the reaction to keep it at a reasonable temperature. Therefore, it is an advantage to first react a stream of sulphuric acid with a stream of ammonia to form ammonium bisulphate ($NH_4HSO_4$). This separates the reaction in two steps and limits the amount of heat given off by each of the two separate steps, making it easier to carry the production on a large scale.

In one embodiment, the second stream of ammonia is regulated so that at most one mole of ammonia is injected in the pre-reactor for each mole of sulphuric acid.

In one embodiment, the second stream of ammonia is regulated so that at least one mole of ammonia is injected in the pre-reactor for each mole of sulphuric acid. In one embodiment, the second stream of ammonia is regulated so that 1.01 to 1.10, in particular 1.02 to 1.07 mole of ammonia is injected for each mole of sulphuric acid injected in the pre-reactor.

When the two components are injected in an equimolar ratio, the stream of sulphuric acid is said to be completely pre-neutralized. When the ratio ammonia to sulphuric acid is below one, the stream of sulphuric acid is only partly pre-neutralized. The stream of water is adjusted to achieve the desired concentration of the final liquid stream of ammonium bisulphate. Water is also used as a mean to control the temperature of the pre-reactor, more water injected in the pre-reactor leads to a lower temperature in the pre-reactor.

In one embodiment, the temperature of the second stream of ammonia is below 10° C. The second stream of ammonia may be used as another mean to control the temperature in the pre-reactor. It may be difficult to increase the stream of water because it is not desired to go below a certain concentration of the liquid stream of ammonium bisulphate, so other cooling means may be necessary. It is fairly easy to adapt an already existing pre-reactor to cool down the second stream of ammonia directed to it. In one embodiment, the temperature of the second stream of ammonia is below 5° C., in particular at about 4° C.

In one embodiment, the pre-reactor is an annular pipe reactor.

In one embodiment, the pipe reactor is an annular pipe reactor. From the prior art cited above, it is known to design a reactor for the production of a urea ammonium-sulphate-based composition where the reactor comprises two annular pipe reactors.

In one embodiment, aluminium sulphate is comprised in the liquid stream of ammonium bisulphate and/or the liquid stream of urea, in particular in the liquid stream of urea. Aluminium sulphate may be used in a reactor for the production of a urea ammonium sulphate-based composition to reduce the viscosity of the streams within the reactor. In the context of this disclosure, aluminium sulphate refers to any kind of solid compound comprising an atom of aluminium and two molecules of sulphate anions. In particular, aluminium sulphate refers to the group comprising anhydrous, hexadecahydrate, heptadecahydrate and octadecahydrate aluminium sulphate, and a double sulphate salt with the generic formula $XAl(SO_4)_2 \cdot 12H_2O$, where X is a mon-ovalent cation, and mixtures thereof. Aluminium sulphate may be introduced in the reactor via the liquid streams directed into the reactor, such as the liquid stream of ammonium bisulphate and the liquid stream of urea. In one embodiment, aluminium sulphate is comprised in the liquid stream of urea. Aluminium sulphate may be introduced into these streams as in a solid form, e.g. powder, or as a solution or suspension in an appropriate liquid medium, which may be water or an organic solvent. In one embodiment, aluminium sulphate is introduced into one of the liquid streams directed into the pipe reactor as an aqueous solution.

In one embodiment, the urea ammonium sulphate-based composition obtained in step d) in the method according to the present disclosure comprises from at least 0.1 to at most 1.0 weight % of aluminium sulphate. It is not necessary to add a high amount of aluminium sulphate to obtain the desired effect on the viscosity of the streams in the pipe reactor. Adding a higher amount would only decrease the overall amount of urea ammonium sulphate in the final composition, thus lowering its agronomical benefits. Alu-minium is not a general nutrient for plants, some may require it, but it is also toxic to other crops.

In one embodiment, the urea ammonium sulphate-based composition obtained in step d) comprises from at least 1 to at most 35 weight % of ammonium sulphate, and from at least 50 to at most 95 weight % of urea, wherein all weight % are based on the total weight of the urea ammonium sulphate-based composition. Most crops require much more nitrogen than sulphur from their fertilizer applications. In a urea ammonium sulphate-based composition, nitrogen is supplied in two different forms: ammonium and urea, while sulphur is provided to the crops as sulphate ions. It is therefore an advantage to produce urea ammonium sulphate-based compositions with a variable amount of ammonium sulphate in them. The final composition may be adapted to the specific crop or market targeted by the production unit. For example, Yara International ASA commercializes two urea ammonium sulphate-based compositions: YaraVera® Amidas™, which contains about 23 weight % of ammonium sulphate and about 76 weight % of urea, and YaraVera® Ureas™, which contains 30 weight % of ammonium sul-phate and about 69 weight % of urea.

In a further aspect the present disclosure provides in a system for producing a urea ammonium sulphate-based composition according to the method as provided herein, wherein said system comprises a pipe reactor comprising at least two mixing zones, a first mixing zone for reacting ammonium bisulphate with an ammonia stream of at least 100° C. to obtain a liquid stream comprising ammonium sulphate and a second mixing zone for reacting ammonium sulphate with urea to obtain a urea ammonium sulphate-based composition.

In a particular embodiment the system as disclosed herein further comprising a pre-reactor fluidly connected to the pipe reactor for preparing ammonium bisulphate by reacting sulphuric acid, water and ammonia.

In a particular embodiment, the system as disclosed herein provides that said pipe reactor and/or said pre-reactor is an annular pipe reactor.

In one embodiment, the system as disclosed herein com-prises means for heating a stream of ammonia gas to at least 100° C. It is understood that said means for heating a stream of ammonia gas is situated upstream of the inlet for ammo-nia in the pipe reactor. In one embodiment, the means for heating a stream of ammonia gas to at least 100° C. is a shell-and-tube heat exchanger. In one embodiment, the shell-and-tube heat exchanger is configured to heat a stream of ammonia gas to at least 100° C., in particular using pressured steam, such as 4 bar pressured steam as heating medium.

In a further aspect the present disclosure provides in the use of an ammonia stream of at least 100° C. for producing a urea ammonium sulphate-based composition in a pipe reactor. In particular the use of an ammonia stream of at least 100° C. to improve the reliability of the production opera-tions in a method for producing a urea ammonium sulphate-based composition in a pipe reactor.

In a particular embodiment the use as disclosed herein provides that said pipe reactor is an annular pipe reactor.

Example 1

The FIGURE represents a reactor for the production of UAS according to the present disclosure comprising a pipe reactor, a pre-mixer and a pre-reactor. The reactor head (1) and reactor body (14) of the pipe reactor is compulsory in all variations of the reactor, while the use of a pre-mixer and/or pre-reactor will be dependent on the process conditions.

The head (1) of the reactor comprises a reaction chamber comprising a first and a second mixing zone. The first mixing zone is the area around the end of the sulphuric acid cone (3A), where the liquid stream of ammonium bisulphate reacts with the first stream of ammonia; and the second mixing zone is located beyond the end of the ammonia cone (2A) where the liquid stream of urea comes into contact with the stream of ammonium sulphate and is mixed with said stream to provide a liquid stream of urea ammonium sul-phate. The head (1) is tubular with a convergent part (1A) at its downstream end. It has an axial sulphuric acid injector (3, 3A) through which a composition comprising (partly) neu-tralized sulphuric acid is axially injected in the pipe reactor. Pre-heated ammonia is introduced tangentially through inlet (8) into an ammonia injector (2) forming a first annular chamber surrounding the acid injector (3, 3A). The ammonia injector (2) has a cone (2A) at its downstream end. An aqueous composition comprising mainly urea (optionally together with other components such as formaldehyde, biuret, ammonium sulphate and ammonia) is supplied through an inlet (7) to a second annular chamber surround-ing the ammonia injector (2). The body (14) of the reactor is the straight length of the reactor downstream of the convergent part (1A). Water may be added to the stream of urea via pipe (13). The aqueous stream of urea also com-prises aluminium sulphate as a viscosity-reducing agent which reduces the viscosity of the UAS solution or slurry. Aluminium sulphate is added to the aqueous urea solution through an inlet (19), which is arranged upstream of the inlet (7). Preferably, the viscosity-reducing agent is added con-tinuously to the aqueous urea composition.

In this embodiment, sulphuric acid is partially neutralized by ammonia before any introduction of urea, in a separate reactor, hereafter called a pre-reactor. The pre-reactor is arranged upstream of the reactor head (1) of a pipe reactor and has an inlet (9) for ammonia and/or ammonium car-bamate to an annular chamber surrounding the axial sulphu-ric acid supply wherein the acid injector (4) has a conical end (4A). Hence, three distinct streams enter the pipe reactor, which streams can be described as a double annulus flow: the (partly neutralized) sulphuric acid/ammonium sul-phate stream is in the centre, the ammonia and/or ammo-nium carbamate stream is in the first, inner, annulus, and the liquid stream of urea to which a viscosity-reducing agent has been added, is in the second, outer, annulus. Such a pipe reactor is called a double annulus pipe reactor.

A pre-mixer (12) is arranged upstream of the pre-reactor and can be used on the sulphuric acid line to dilute the sulphuric acid flow (5) with water (13) or with scrubbing solution (11) from a scrubbing section, comprising mainly water and ammonium sulphate.

First, the ammonia introduced in inlet (8) was pre-heated at 100° C. The pressure at the top of the pipe reactor was measured to be 5.89 bar. Later, the temperature of the ammonia at inlet (8) was adjusted to 120° C., and the pressure at the top of the reactor dropped to 5.11 bar. This pressure is more suitable for continuous operations of the pipe reactor.

The invention claimed is:

1. A method for producing a urea ammonium sulphate-based composition in a pipe reactor comprising a first and a second mixing zone, the method comprising the steps of:
   a) directing a liquid stream comprising ammonium bisul-phate to the first mixing zone of the pipe reactor;
   b) directing a first stream of ammonia to the first mixing zone of the pipe reactor for reacting with the liquid stream comprising ammonium bisulphate, provided in step a), to obtain a liquid stream comprising ammo-nium sulphate;
   c) directing the liquid stream comprising ammonium sulphate, provided in step b), to the second mixing zone of the pipe reactor; and
   d) directing a liquid stream of urea to the second mixing zone of the pipe reactor for mixing with the liquid stream comprising ammonium sulphate, provided in step b), to obtain a urea ammonium sulphate-based composition;

wherein in step b), the first stream of ammonia is pre-heated to a temperature of at least 100° C. prior to being directed to the first mixing zone of the pipe reactor.

2. The method according to claim 1, further comprising, in step a), preparing the liquid stream comprising ammo-nium bisulphate in a pre-reactor fluidly connected to the pipe reactor, by reacting a stream of sulphuric acid, a stream of water and a second stream of ammonia.

3. The method according to claim 2, wherein the tem-perature of the second stream of ammonia directed in the pre-reactor is below 10° C.

4. The method according to claim 2, wherein the pre-reactor is an annular pipe reactor.

5. The method according to claim 1, wherein the pipe reactor is an annular pipe reactor.

6. The method according to claim 1, wherein the liquid stream of ammonium bisulphate and/or the liquid stream of urea comprises aluminium sulphate.

7. The method according to claim 6, wherein the urea ammonium sulphate-based composition obtained in step d) comprises from at least 0.1 to at most 1.0 weight % of aluminium sulphate.

8. The method according to claim 1, wherein the tem-perature of the first stream of ammonia directed to the first mixing zone of the pipe reactor is at least 120° C.

9. The method according to claim 1, wherein the urea ammonium sulphate-based composition obtained in step d) comprises from at least 1 to at most 35 weight % of ammonium sulphate, and from at least 50 to at most 95 weight % of urea, wherein all weight % are based on the total weight of the urea ammonium sulphate-based compo-sition.

10. The method according to claim 6, wherein the liquid stream of urea comprises aluminium sulphate.

* * * * *